US012668838B2

(12) United States Patent (10) Patent No.: US 12,668,838 B2
Pinard et al. (45) Date of Patent: Jun. 30, 2026

(54) GENE SPECIFIC SPATIAL ROLLING CIRCLE AMPLIFICATION AND NGS SEQUENCING

(71) Applicant: Miltenyi Biotec B.V. & Co. KG, Bergisch Gladbach (DE)

(72) Inventors: Robert Pinard, Bergisch Gladbach (DE); Seiyu Hosono, Bergisch Gladbach (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 421 days.

(21) Appl. No.: 18/210,119

(22) Filed: Jun. 15, 2023

(65) Prior Publication Data

US 2023/0407383 A1     Dec. 21, 2023

(30) Foreign Application Priority Data

Jun. 20, 2022     (EP) .................................... 22179807

(51) Int. Cl.
*C12Q 1/6869* (2018.01)
*C12Q 1/6862* (2018.01)
(52) U.S. Cl.
CPC ......... *C12Q 1/6869* (2013.01); *C12Q 1/6862* (2013.01)

(58) Field of Classification Search
CPC .. C12Q 1/6869; C12Q 1/6862; C12Q 1/6841; C12Q 1/6844
See application file for complete search history.

(56) References Cited

FOREIGN PATENT DOCUMENTS

WO     WO-2018045181 A1 *   3/2018   ......... C12N 15/1093
WO     WO 2019/199579     10/2019
WO     WO 2020/076976     4/2020

OTHER PUBLICATIONS

EP Extended European Search Report in European Appln. No. 23178590.8, mailed on Nov. 22, 2023, 7 pages.
Gyllborg et al., "Hybridization-based in situ sequencing (HybISS) for spatially resolved transcriptomics in human and mouse brain tissue," Nucleic Acids Research, Nov. 2020, 48(19):e112, 11 pages.

* cited by examiner

*Primary Examiner* — Stephen T Kapushoc
*Assistant Examiner* — Kailey Elizabeth Cash
(74) *Attorney, Agent, or Firm* — Fish & Richardson P.C.

(57)     ABSTRACT
The invention is directed to a method to simultaneously obtain both the spatial location and sequence information of a target sequence with a higher resolution than the known technologies. The method comprises steps to spatially localize the mRNA expressed on a tissue by the use of a hybrid circular/linear DNA probe with a UMI and, after several amplification steps, obtaining the sequence information by NGS.

8 Claims, 7 Drawing Sheets

GENE SPECIFIC SPATIAL ROLLING CIRCLE AMPLIFICATION AND NGS SEQUENCING

CROSS-REFERENCE TO RELATED APPLICATIONS

This application claims the benefit of European Patent Application No. 22179807.7, filed Jun. 20, 2022, the entire contents of which is incorporated herein by reference in its entirety.

FIELD OF INVENTION

This invention describes the method for recognizing and amplifying a specific region on a messenger RNA using a locator circle (or open circle that are ligated later) containing Unique Molecular Identifier (UMI) probe followed by reverse transcription of a region of interest which contains a mutation or sequence variant and copying the sequence information of the UMI. The resulting cDNA with UMI information is retrieved, extracted, and sequenced by NGS of the Rolling Circle Amplified (RCA) product generated on a tissue section.

BACKGROUND

It is challenging to detect all expressed genes on a sub cellular level on tissue and simultaneously obtain the sequence and/or spatial information of these genes. WO2020076976 discloses a method to obtain the sequence information of nucleic acids including the spatial location by FISSEQ. WO2019199579 teaches a snail probe system for a similar purpose.

SUMMARY OF THE INVENTION

Accordingly, it was an object of the invention to provide a method to simultaneously obtain both the spatial location and sequence information of a target sequence with a higher resolution than the known technologies.

Here we describe a method to
(1) Spatially localize the mRNA expressed on a tissue by the use of a hybrid circular/linear DNA probe with UMI.
(2) The nucleotide information of an adjacent region downstream from the region where the circular/linear DNA probe with UMI anneals is copied with reverse transcriptase. Concurrently the circle portion of the hybrid probe which carried a UMI sequence can be copied by Phusion DNA polymerase and the resulting copied RNA strand is ligated to the reverse transcribed cDNA.
(3) The UMI containing cDNA strand is then extracted from the tissue
(4) The extracted UMI containing cDNA strand is then PCR amplified with a PCR primer with a known adaptor ends.
(5) The PCR product is circularized and RCA amplified
(6) The RCA product can be sequenced by NGS.

Object of the invention is a method to obtain the spatial location and sequence information of a target sequence of at least one m-RNA strand on a tissue sample comprising the steps:
a. providing a locator probe, comprising a) a linear locator hybridized to a circular locator via a locator anchor region capable of binding the circular locator and b) a RNA anchor region capable of binding to at least one m-RNA strand and c) a primer sequence; and wherein the circular locator comprises a UMI region, a first and a second primer region and a region complementary to the locator anchor region of the linear locator;
b. hybridizing the locator probe with the RNA anchor region to the m-RNA strand;
c. complementing the RNA anchor region of the locator probe using the m-RNA strand as template thereby obtaining a reversed transcribed c-DNA strand;
d. complementing the circular locator starting from the first primer region using the circular locator as template and ligating the resulting oligomer with the locator anchor region of the linear locator thereby obtaining an extended reversed transcribed c-DNA strand comprising the UMI region and the target sequence of the m-RNA strand;
e. multiplying the circular locator by RCA starting from the second primer region on the tissue sample creating at least one first rolony (only one L);
f. spatially resolution sequencing the at least one first rolony thereby obtaining the spatial and sequence information of the at least one first rolony (or in other words: obtaining the spatial coordinates and the circular locator UMI by sequencing of at the at least one first rolony);
g. removing the extended reversed transcribed c-DNA strand from the tissue and de-hybridizing the extended reversed transcribed c-DNA strand from the m-RNA strand obtaining a single stranded oligomer;
h. providing the single stranded oligomer with a first and a second adaptor primer at the 3' and 5' ends obtaining a primed single stranded oligomer, amplification of the primed single stranded oligomer by PCR and circularization of the primed single stranded oligomers by ligation of the first and second adaptor primer with each other thereby creating a circular single stranded oligomers; and
i. multiplying the circular single stranded oligomer by RCA into second rolonies; sequencing the second rolonies and linking the spatial information of the first rolonies with the sequence information of the second rolonies via the UMI sequence.

The present invention is directed to a method of performing a spatial localization of a gene of interest in a given tissue using a hybrid probe which contains either a circular (FIG. 1A) or open-circular molecule (FIG. 1B) with a random and not predefined unique molecular identifier (UMI) and two priming regions. The circle/open-circle can be either pre-attached to a linear DNA primer (FIGS. 1A and 1B) or the circle locator can be hybridized to the linear DNA primer after the linear primer attaches to the sequence upstream of a desired region on an mRNA directly on a tissue (FIG. 1C). The circular portion of the hybrid probe can then be amplified by rolling circle amplification (RCA) using an oligonucleotide primer directly on a tissue resulting in an RCA product occurring at the exact location where the mRNA was expressed on a given tissue. The random and not pre-defined UMI can then be decoded by sequencing the RCA product.

Next, the desired sequence information of the particular region of interest which certain nucleotide change or variant on the same mRNA which was spatially localized on a tissue then can be simultaneously captured by reverse transcription of the mRNA by the same hybrid probe as a primer.

Concurrently with the reverse transcription, the UMI information can be captured on the same reverse transcribed cDNA strand by Phusion™ DNA Polymerase which is initiated by a DNA primer specifically designed to copy the circular strand. Once the Phusion™ DNA Polymerase has copied the DNA circle, it can then be ligated onto the same cDNA strand which captured the sequence information in the region of interest. If an open circle locator probe is used, it is ligated to make a closed circle at this point.

The cDNA with a UMI ligated is then physically retrieved and extracted from the tissue.

The retrieved cDNA is then PCR amplified using a PCR primer which anneals to the 5' and 3' end of the cDNA and carries DNA adapters.

The PCR amplified product can then be circularized using the splint bridge oligonucleotide primer which brings the two ends together.

The circle is then amplified by Rolling Circle Amplification (RCA). The RCA product is then sequenced.

By NGS sequencing the spatial identifier UMI and the linked mRNA sequence of interest can be assigned to the tissue location.

By NGS sequencing the targeted region of interest on genomic DNA or mRNA, mutation or nucleotide variant can be analyzed.

DESCRIPTION OF THE DRAWINGS

FIG. 1B shows the open circle version of this probe, where the locator circle can be closed later during the process by T4 DNA Ligase. FIG. 1C shows the version where the linear probe is hybridized to the target first, and followed by Reverse Transcription. Once the linear probe is attached stably to the target, then the circle locator is hybridized to the linear probe. For all three designs, the 3' half of the linear probe has a sequence which anneals to a specific region in the target mRNA gene upstream from the region of interest which needs to be sequenced. The region of interest will contain a sequence suspected of nucleotide change of variant difference.

In FIG. 2A, a hybrid closed open circle locator/linear hybrid probe is used to reverse transcribe the mRNA region of interest into cDNA. Subsequently, the locator circle containing a UMI is copied and ligated to the cDNA and the locator circle is closed. In FIG. 2B, the close locator circle is amplified by RCA and the UMI portion is sequenced in situ. The cDNA strand ligated containing a copied UMI is then extracted for sequencing of the region of interest.

DETAILED DESCRIPTION

Spatial localization of mRNA molecule by RCA followed by ex-situ sequencing of the region of interest from the same RNA molecule involves RCA performed directly on tissue consists of a 9 step process. (1) Hybridization of the linear or linear/circular locator probe to mRNA on tissue. (2) Reverse transcription of the downstream mRNA region of interest by the linear portion of the hybrid locator probe which hybridized to the target mRNA molecule (2A) and DNA replication of the circular portion of the hybrid probe by Phusion DNA polymerase with a circle specific oligonucleotide primer (2B). (3) T4 DNA ligation to connect the copied circle UMI and the cDNA. When an open circle locator is used, it is ligated at this step as well. (4) RCA with a circle specific RCA primer to generate rolonies (DNA concatemers nanoballs) and sequencing in situ of the rando UMI on the generated rolonies. (5) Extraction of cDNA-UMI first strand from tissue. (6) 2nd strand cDNA Synthesis. (7) PCR amplification of the cDNA with P1/P2 adaptor primers. (8) Circularization of the PCR amplified product and RCA amplification of the circle which contains UMI and the region of interest. (9) NGS Sequencing and identification of the location and the sequences of the region of interest by matching with the UMI.

In a first embodiment of the invention circular locator is provided in step a) as closed circle. In another embodiment, the circular locator is provided in step a) with as open circle and wherein the 3' and 5' ends of the open circle are ligated with each other creating a circular locator before multiplying the circular locator in step d).

In the embodiment with the open circle, the 3' and 5' ends of the open circle may be ligated with each other with a T4 DNA Ligase, wherein the second primer region of the circular locator acts as a bridge splint.

Step d) (complementing the circular locator) may be performed by Phusion™ DNA Polymerase using the first primer region of the circular locator as the initiator primer. Further, the ligation step in step d) can by performed by a DNA ligase.

The locator probe may be provided in the following variants:

by first hybridizing the linear locator to the circular locator.

by first hybridizing the linear locator to the to at least one m-RNA strand and then hybridizing the circular locator to the linear locator.

by first hybridizing the linear locator to the to at least one m-RNA strand, complementing the RNA anchor region of the locator probe into a reversed transcribed c-DNA strand and then hybridizing the circular locator to the linear locator.

Preferable, the single stranded oligomer is physically sheared to smaller fragment before adding a first and a second adaptor primer at the 3' and 5' ends.

Figures 1A, 1B, 1C:
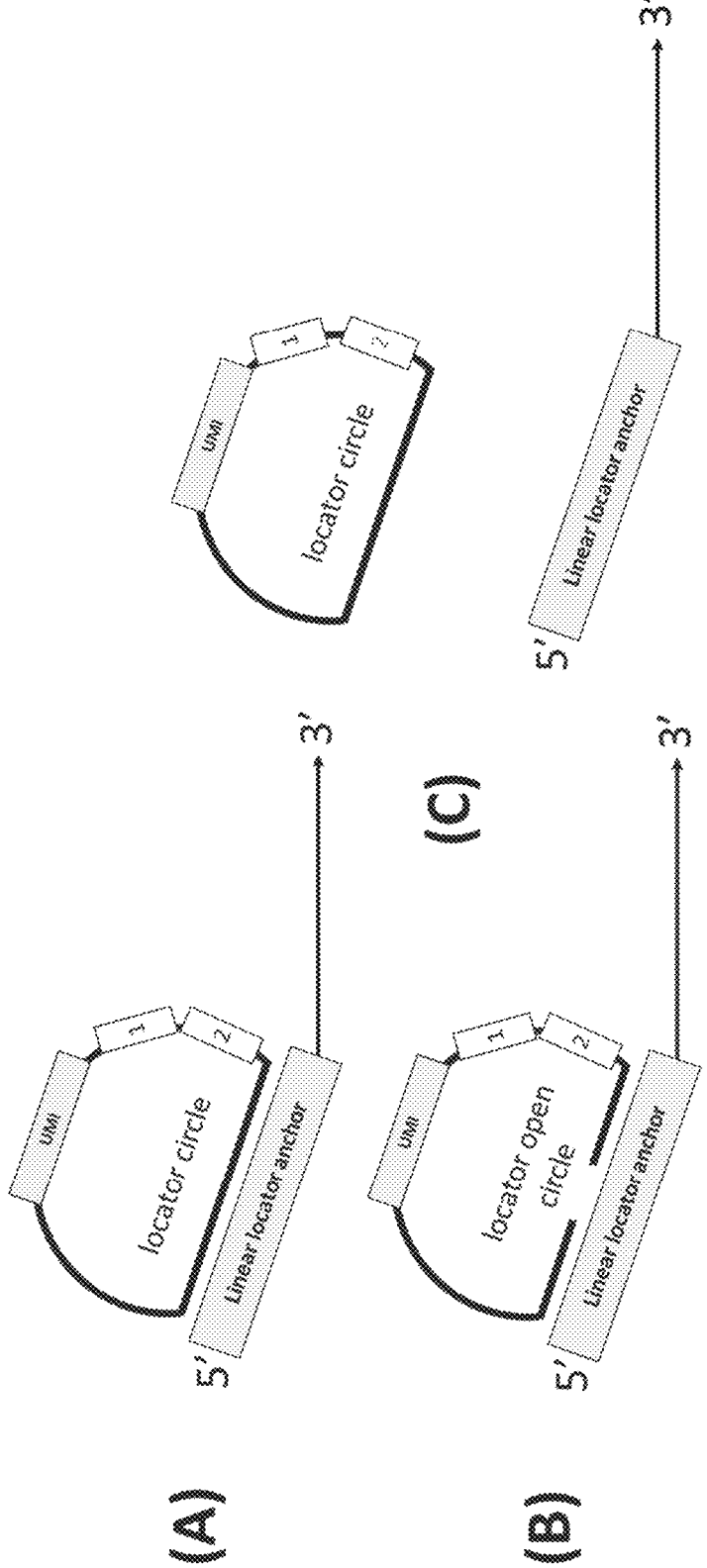
FIGS. 1A-1C show three embodiments of the hybrid circular/linear locator probe. The closed circular portion (FIG. 1A) contains a random UMI sequence, two priming regions 1 & 2 and an anchor sequence which is annealed to the 5' half of the linear locator probe portion probe.

These embodiments are shown in the drawings. FIGS. 1A-1C show the three possible designs of the locator probe set up. In FIG. 1A, a hybrid locator probe is produced by hybridizing a circular probe which contains UMI and a linear probe which is pre-bound to the circle through the Region of Interest Specific Sequence (SP). In FIG. 1B, an open circle probe is used. In both FIGS. 1A and 1B, the preassembled probes are stable and purified prior to usage. In FIG. 1C, the linear probe is used first and the locator circle is added after the linear probe hybridizes to the mRNA target. The size of the circle can be between 20 to 400 bp long with the region of interest SP portion to be about 10-40 bp to form a stable double stranded structure with the linear probe. The 3' end of the linear probe consists of sequence about 30 bp long which can hybridize to a specific region in an mRNA target of interest on tissue.

Figure 2A:
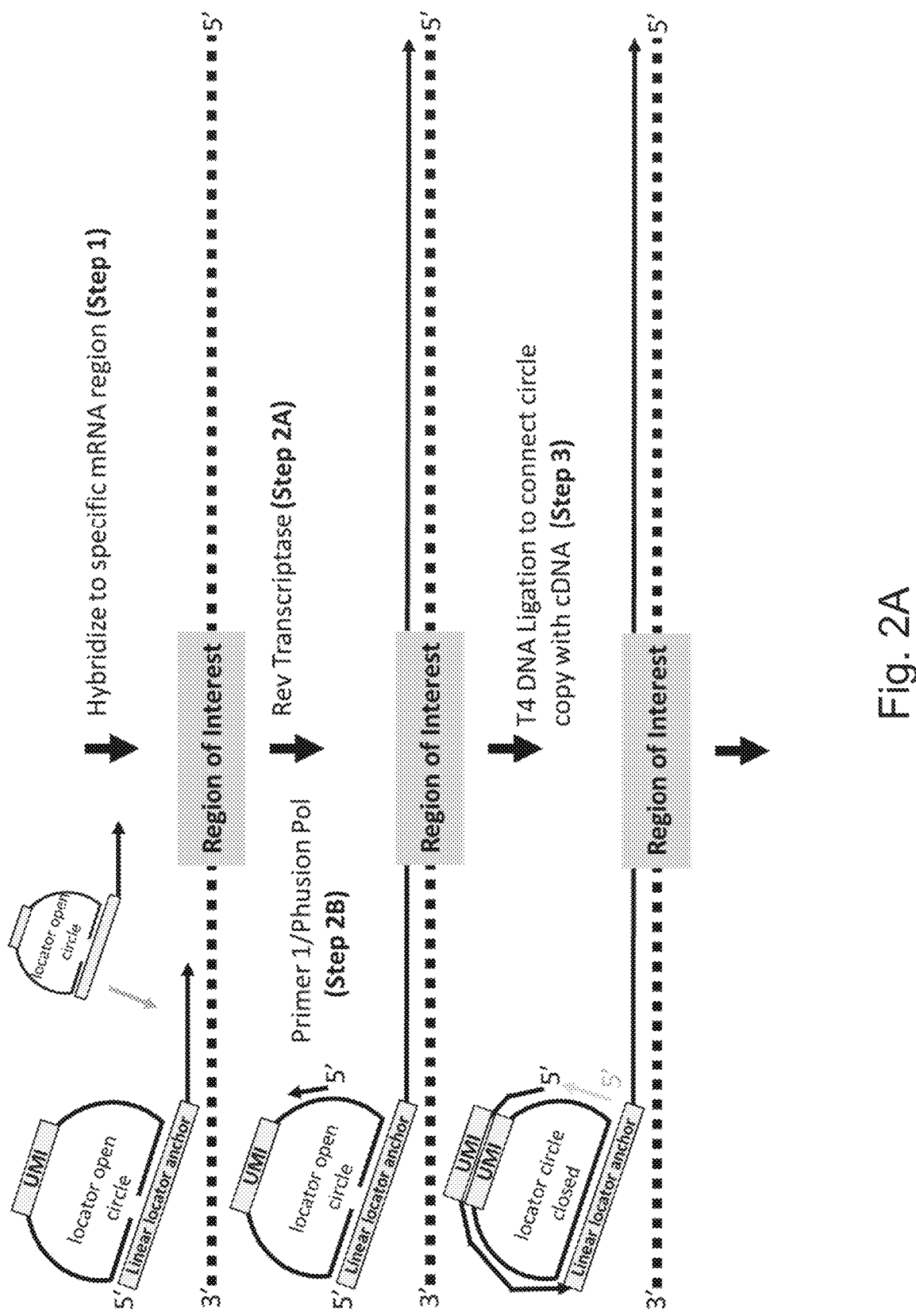
FIGS. 2A and 2B show how the hybrid locator probe binds to a region upstream from the region of interest in a particular mRNA and reverse transcribe the region of interest.
Figure 2B:
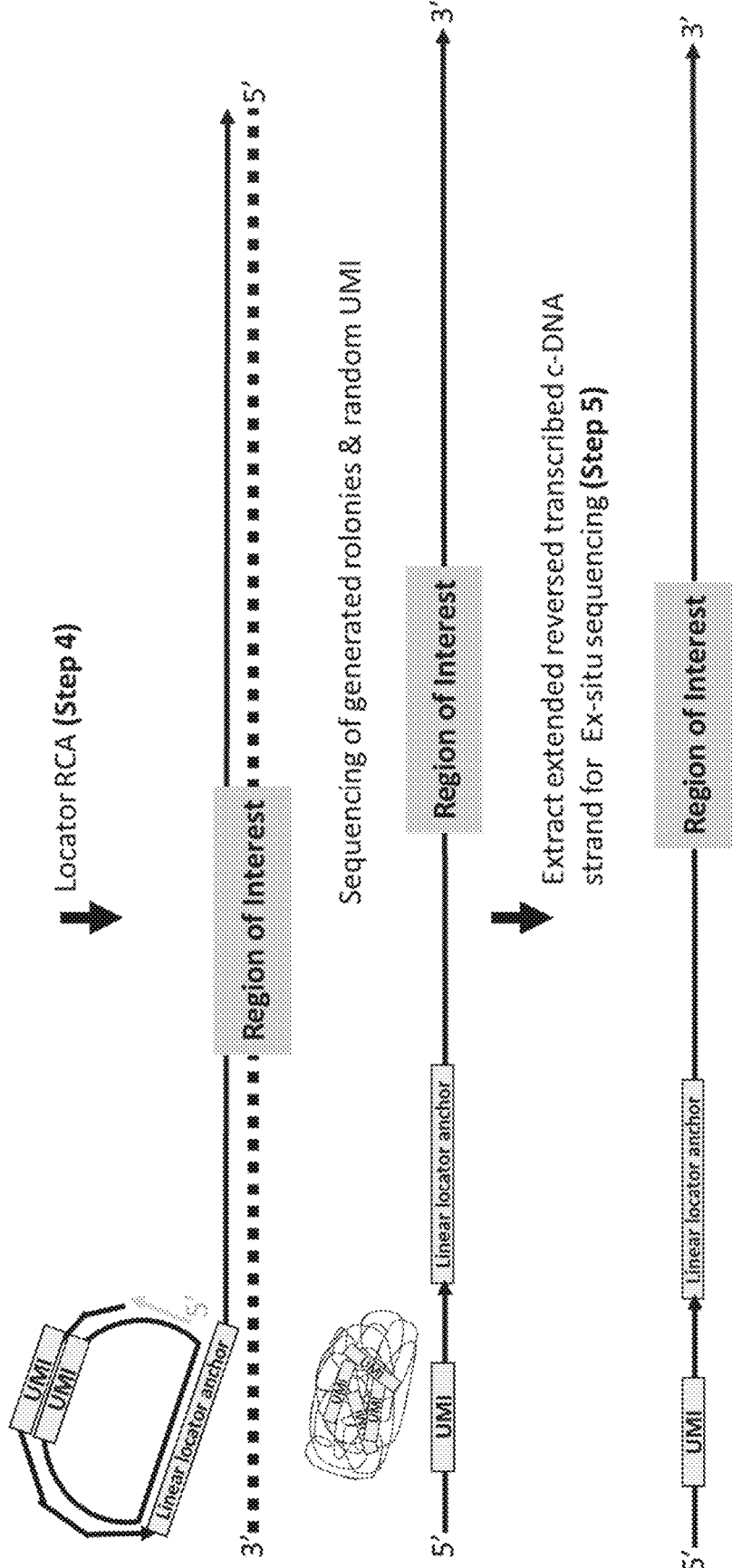

FIGS. 2A and 2B show the process of how the locator probes are used. In Step 1, in a fixed tissue on a slide, the hybrid locator probe is added and binds to a region upstream from the region of interest in a particular mRNA (dotted line). In one embodiment of the invention, the linear probe, in step 1, is added first and binds to a region upstream from the region of interest in a particular mRNA (dotted line) and the circle added later.

Next in Step 2A, reverse transcription of the region of interest is initiated by the locator probe, that is used as a primer. However in one embodiment, the circle locator is added to hybridize to the linear probe anchor region only once the reverse transcription is complete. Next in Step 2B, the DNA synthesis of the locator circle is initiated by a circle specific primer that binds to the primer 1 region.

Next, the locator circle is copied by a non strand-displacement enzyme for example Phusion DNA polymerase and it is then connected to the reverse transcribed cDNA strand by T4 DNA ligation (Step 3). If an open circle locator probe version is used, the circle is closed by T4 DNA ligation at this step as well.

Next, isothermal rolling circle amplification (RCA) of the locator circle is performed on the tissue with Phi29 DNA polymerase and RCA oligonucleotide binding to primer region 2 (Step 4). The resulting location of the RCA product on the tissue is determined by sequencing the randomly generated UMI on tissue and obtaining the coordinates.

Figure 3:
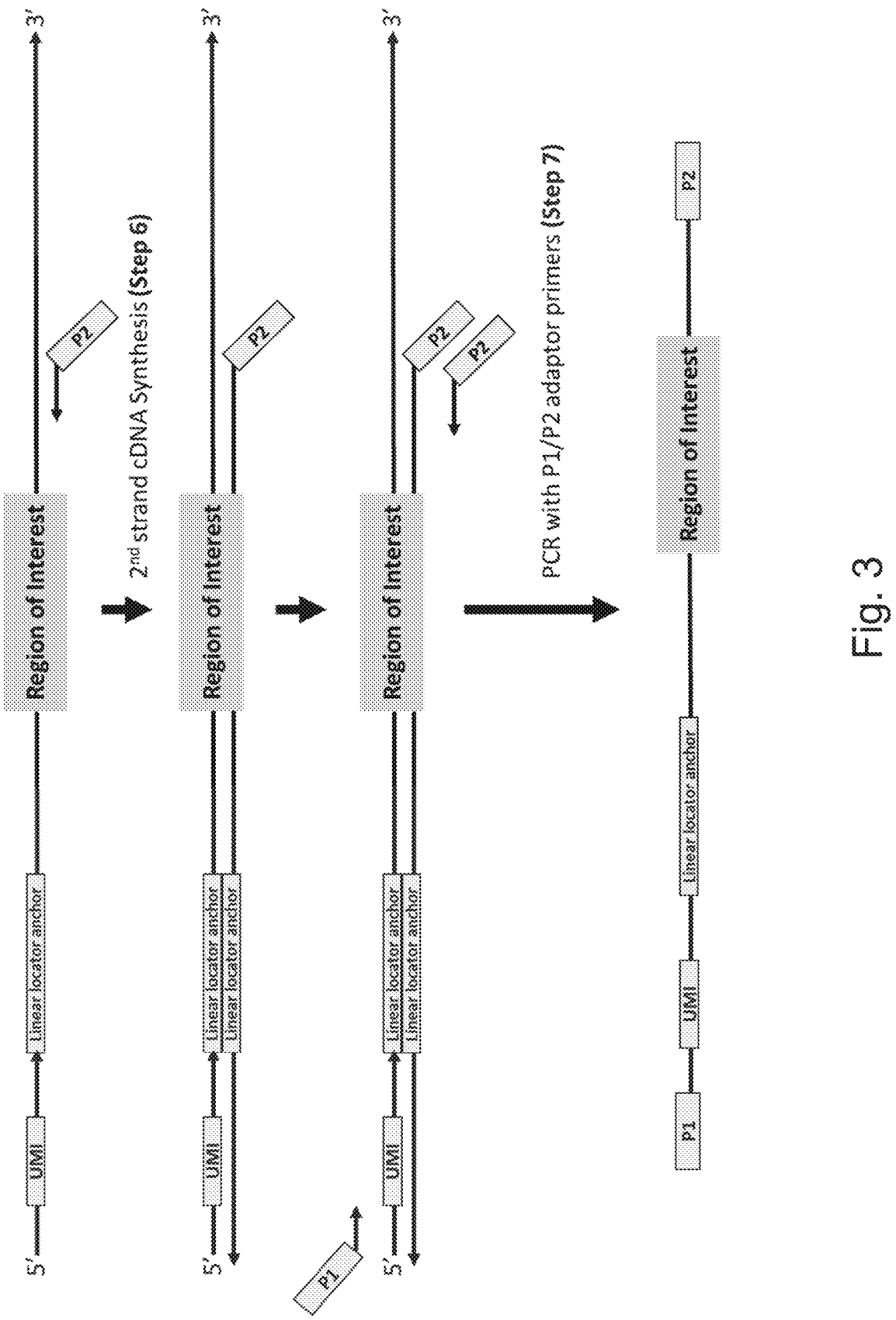
FIG. 3 shows how the locator circle which contains the UMI region and the Region of Interest specific sequence can be amplified by PCR prior to sequencing.

Next in Step 5, the cDNA is extracted from the tissue after the locator circle RCA has been visualized FIG. 3 describes the workflow after the $1^{st}$ strand cDNA is extracted from the tissue section slide. Once the cDNA has been extracted from the tissue and purified, 2n d strand of cDNA (Step 6) and subsequent PCR reaction (Step 7) are performed using a pair of primers P1 and P2. Primer P1 is located upstream of the circle locator region and Primer P2 is located downstream of the "Region of Interest."

Figure 4:
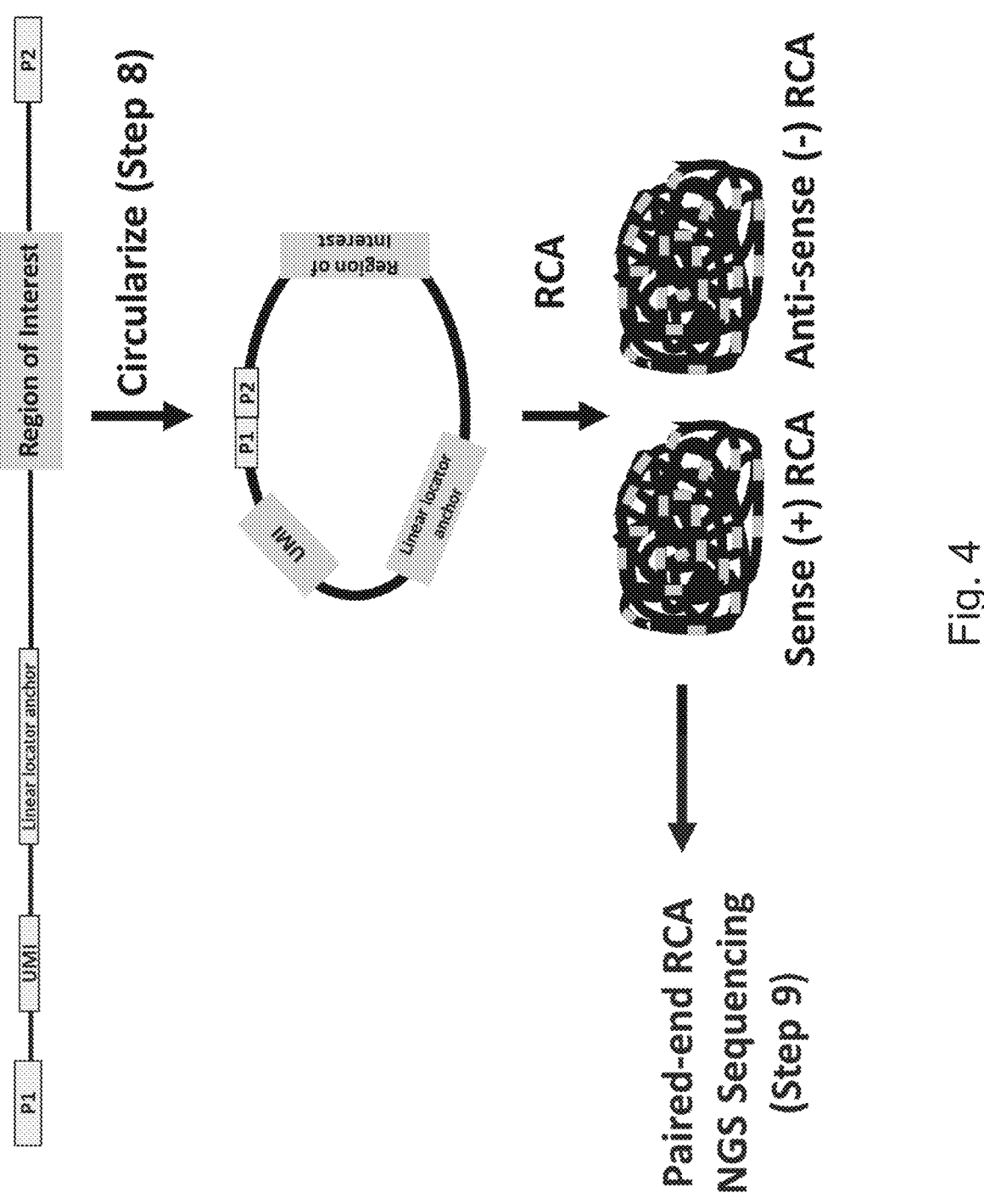
FIG. 4 shows how the extracted cDNA strand from the tissue can be PCR amplified and later circularized by adding adaptor regions (P1 and P2) to the PCR primers.

FIG. 4 describes the workflow to generate RCA product to be sequenced by NGS. In Step 8, the PCR product library is used to generate circle and generate RCA product and used for sequencing to identify the UMI and is correlated to the DNA sequence of the region of interest. In Step 9, RCA of both sense and anti-sense strand can be generated independently using a sense and anti-sense bridge guide.

Figure 5:
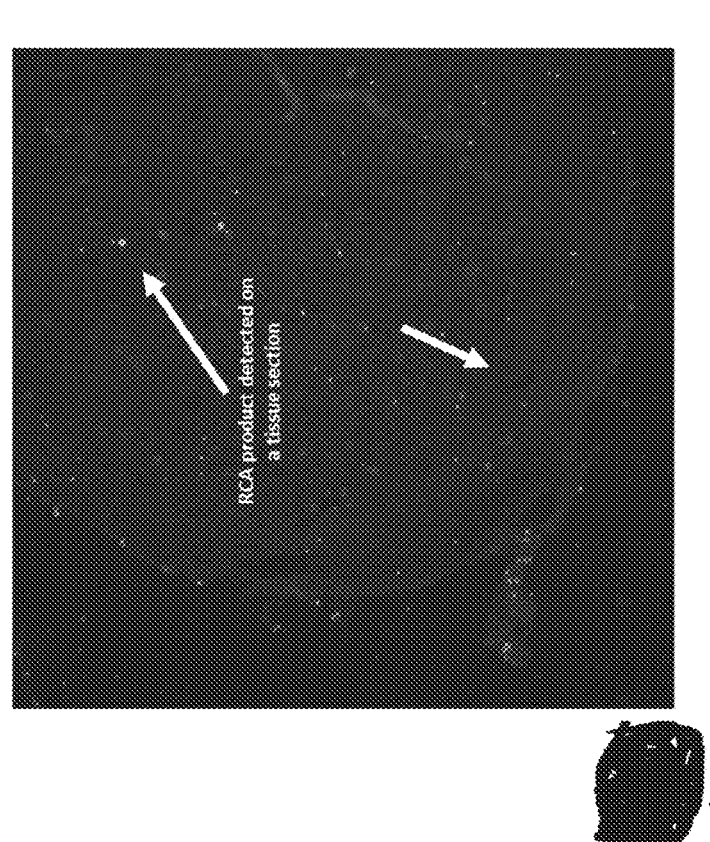
FIG. 5 shows how the PCR amplified product with P1/P2 adaptor ends can be circularized and RCA amplified to be analyzed by NGS sequencing.
Figure 5:
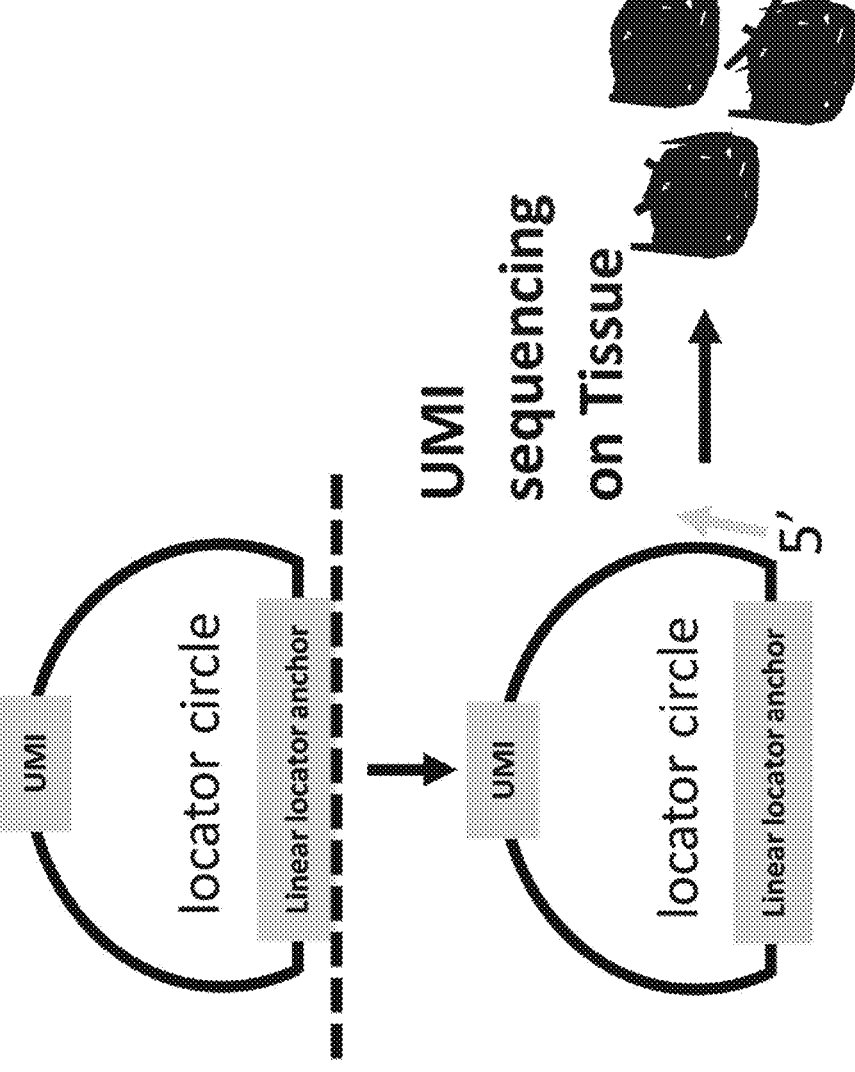

FIG. 5 shows an example of UMI sequencing of rolonies on a tissue section.

Figure 6:
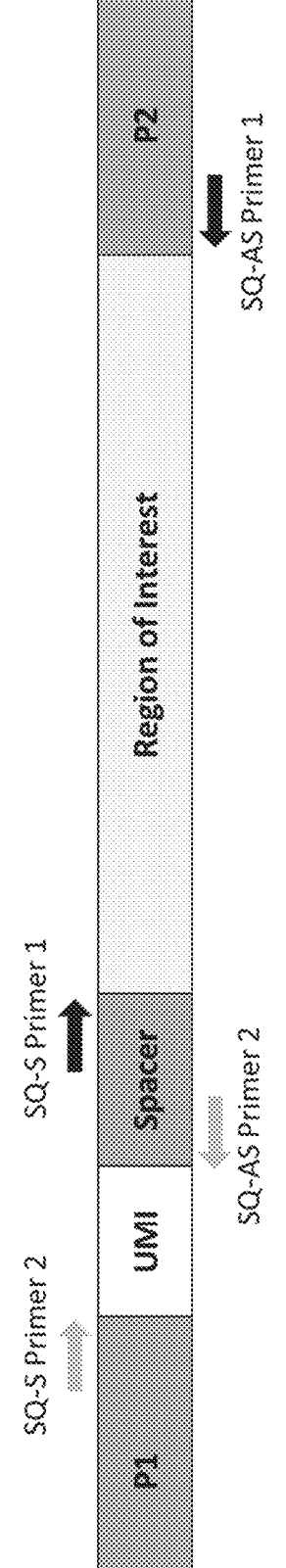
FIG. 6 describes the primers necessary to perform paired-end sequencing to match and pair the UMI region and the "region of interest.

FIG. 6 describes the primers necessary to perform paired-end sequencing to match and pair the UMI region and the "region of interest." First segment of the paired-end sequencing is performed for the region of interest with Paired end segment 1 sequencing primers, SQ-S Primer 1 and SQ-AS Primer 1. The second segment of the paired-end sequencing is performed for the UMI region with Paired end segment 2 sequencing primers, SQ-S Primer 2 and SQ-AS Primer 2.

NGS sequencing can determine either a mutation/nucleotide variant exists in the target region of interest and by sequencing the UMI, the location of each rolony on the substrate can later be correlated with the original position of the tissue. That means the location of the gene on the tissue can be determined and it can be checked if the gene had a mutation or not via sequencing.

What is claimed is:

1. A method to obtain the spatial location and sequence information of a target sequence of at least one m-RNA strand on a tissue sample comprising the steps:
   a. providing a locator probe, the locator probe comprising:
      i) a linear locator having a locator anchor region and an RNA anchor region capable of binding to the at least one m-RNA strand; and
      ii) a circular locator having a primer sequence with a first and a second primer region, a UMI region, and a region complementary to the locator anchor region of the linear locator;
   b. hybridizing the RNA anchor region of the locator probe to the m-RNA strand;
   c. extending the RNA anchor region of the locator probe using the m-RNA strand as template thereby obtaining a reverse transcribed c-DNA strand;
   d. complementing the circular locator starting from the first primer region using the circular locator as template and ligating the resulting oligomer with the locator anchor region of the linear locator thereby obtaining an extended reverse transcribed c-DNA strand comprising the UMI region and the target sequence of the m-RNA strand;
   e. multiplying the circular locator by RCA starting from the second primer region on the tissue sample creating at least one first rolony;
   f. performing spatial resolution sequencing on the at least one first rolony thereby obtaining the spatial and sequence information of the at least one first rolony;
   g. removing the extended reverse transcribed c-DNA strand from the tissue and de-hybridizing the extended reverse transcribed c-DNA strand from the m-RNA strand obtaining a single stranded oligomer;
   h. providing the single stranded oligomer with a first and a second adaptor primer at the 3' and 5' ends obtaining a primed single stranded oligomer, amplifying the primed single stranded oligomer by PCR and circularizing the primed single stranded oligomer by ligation of the first and second adaptor primer with each other thereby creating a circular single stranded oligomer; and
   i. multiplying the circular single stranded oligomer by RCA into second rolonies; sequencing the second rolonies and linking the spatial information of the first rolonies with the sequence information of the second rolonies via the UMI sequence.

2. The method of claim 1, wherein the circular located is provided in step a) as a closed circle.

3. The method of claim 1, wherein the circular locator is provided in step a) as an open circle and wherein the 3' and 5' ends of the open circle are ligated with each other before multiplying the circular locator in step d).

4. The method of claim 1, wherein the ligation step in step d) is performed by a DNA ligase.

5. The method of claim 1, wherein the linear locator is hybridized to the circular locator via the locator anchor region of the linear locator before hybridizing the locator probe to the m-RNA strand.

6. The method of claim 1, wherein the linear locator of the locator probe is hybridized to the m-RNA strand before the linear locator is hybridized to the circular locator via the locator anchor region of the linear locator.

7. The method of claim 6, wherein the locator probe is provided by first hybridizing the linear locator to the at least one m-RNA strand, extending the RNA anchor region of the linear locator into a reverse transcribed c-DNA strand and then hybridizing the circular locator to the linear locator.

8. The method of claim 1, wherein the single stranded oligomer is physically sheared into smaller fragments before adding a first and a second adaptor primer at the 3' and 5' ends.

* * * * *